United States Patent [19]
Zengel et al.

[11] 3,931,210
[45] Jan. 6, 1976

[54] PRODUCTION OF P-AMINOBENZOIC ACID

[75] Inventors: Hans-Georg Zengel, Kleinwallstadt; Manfred Bergfeld, Erlenbach, both of Germany

[73] Assignee: Akzo N.V., Arnhem, Netherlands

[22] Filed: Mar. 13, 1974

[21] Appl. No.: 450,673

[30] Foreign Application Priority Data
Mar. 19, 1973 Germany............................ 2313580

[52] U.S. Cl............................................. 260/518 R
[51] Int. Cl.$^2$...................................... C07C 101/56
[58] Field of Search ................................ 260/518 R

[56] References Cited
OTHER PUBLICATIONS
Theilheimer, W. Synthetic Methods of Organic Chemistry, Vol. 7, (1953), Pub. by S. Karger –N.Y. p. 198 Relied on.
Theilheimer, W. Synthetic Methods of Organic Chemistry, Vol. 11 (1957) Pub. by S. Karger –N.Y. p. 249 Relied on.

*Primary Examiner*—Lorraine A. Weinberger
*Assistant Examiner*—L. A. Thaxton
*Attorney, Agent, or Firm*—Johnston, Keil, Thompson & Shurtleff

[57] ABSTRACT

A two-stage process for producing para-aminobenzoic acid by first reacting certain lower alkyl or glycol monoesters of terephthalic acid or specific salts thereof or mixtures thereof with ammonia in liquid phase at elevated temperatures and pressures to obtain a terephthalic acid monoamide intermediate, removing substantially all ammonia from this intermediate and then converting it into the para-aminobenzoic acid product by the Hofmann reaction, preferably using a sodium hypochlorite solution. The para-aminobenzoic acid, either as the free acid or in the form of its salts or esters is a known product having many uses.

16 Claims, No Drawings

PRODUCTION OF P-AMINOBENZOIC ACID

It is known to produce p-amino-benzoic acid by reduction of p-nitro-benzoic acid. As the reducing agent, one can use tin with hydrochloric acid [Wilbrand et al, Liebigs Anm. 128 (1863), p. 264; Widnmann, Liebigs Anm. 193 (1878), p. 323]. It is also possible to hydrogenate p-nitro-benzoic acid in the presence of platinum oxide in alcohol at 20°–30°C. and 2.5–3 atm. [Adams et al., Journ. Am. Chem. Soc. 49 (1927), p. 1095] or in aqueous methanol on a platinum catalyst in the presence or absence of sodium hydroxide [C.A., 50 (1956), 12618]. According to the process of U.S. Pat. No. 2,947,781, the p-nitro-benzoic acid may be hydrogenated in the form of its approximately 8% by weight aqueous suspension in the presence of platinum, palladium or their oxides as catalysts, at normal pressure and at temperatures in a range of 50°–95°C. According to the process of U.S. Pat. No. 3,324,175, the p-nitrobenzoic acid is hydrogenated in the form of a 30–50% by weight aqueous solution of a mixture of its ammonium and sodium salts, the reaction being carried out at a pH of 7–7.5, a temperature of 80° to 120°C. and at pressures of about 8 to 43 atmospheres gauge, this process using as catalysts either platinum, palladium or their oxides on charcoal or another porous material. As the hydrogenation catalyst, there may also be used Raney nickel [C.A. 53 (1959), 280], especially together with chloroplatinic acid as a promoter [Scholnik et al, Journ. Am. Chem. Soc. 63 (1941), 1192]. In place of the p-nitro-benzoic acid, it is also possible to use its alkali metal salts or esters [C.A. 46 (1925), 469 and also Scholnik et al, supra]. Furthermore, the hydrogenation of the p-nitro-benzoic acid can also be accomplished by using iron catalysts; e.g. iron/hydrochloric acid, with iron (II) sulfate in aqueous ammonia [Lewis et al., Journ. Am. Chem. Soc. 43 (1921) 2118], with iron powder in aqueous ammonium chloride solution at 95°C. [C.A. 54 (1960), 20926] or with iron filings in aqueous soda solution [C.A. 57 (1962), 7158]. It is further known to reduce p-nitro-benzoic acid by means of ammonium sulfide [G. Fischer, Liebigs Ann. 127 (1862), 142] or by means of sodium hydrogen sulfide [Japanese Pat. No. 109,708; C.A. 29 (1935), 4776]. According to the process described in U.S. Pat. No. 3,223,729, the reaction solution obtained in the reduction of the p-nitro-benzoic acid by means of sodium sulfide or sodium hydrogen sulfide is treated with sulfur dioxide until it exhibits a pH value of 7.0 to 3.5 and the free base precipitates. The p-nitro-benzoic acid can also be reduced to the p-aminobenzoic acid by means of elementary silicon in alkaline solution [Meier et al, Ber. 89 (1956), 2301] and by means of sodium borohydride in the presence of metal catalysts [French Pat. No. 1,242,932; Neilson, Journ. Amer. Chem. Soc. (1962), 371]. Also, hydrazine hydrate [Müller et al., Journ. Prakt. Chem. 2, 111, 281], and hydrazine in the presence of palladium on aluminum oxide (U.S. Pat. No. 2,768,209) or in the presence of palladium on active carbon [C.A. 50 (1958), 10668], as well as diethanolamine [Meltsner et al., Journ. Chem. Soc. 62 (1940), 991] facilitate the reduction of p-nitrobenzoic acid to p-aminobenzoic acid.

It is also known to carry out an electrochemical reduction of p-nitrobenzoic acid, for example in a hydrochloric acid solution in the presence of a little $SnCl_2·2H_2O$ as catalyst and with the use of a tin or lead cathode [Ravenscroft et al., Trans. Electrochem. Soc. 84 (1943), 145] or in aqueous ethanolic sulfuric acid with the use of a mercury cathode [Guyader et al., Compt. Rend. (1961),2544]. Also, the photochemical reduction of p-nitro-benzoic acid is known [Japanese Pat. No. 70, 20,888; C.A. 73 (1970), 66246].

For the production of p-aminobenzoic acid, one can also proceed from aceto-p-toluidide which is easily accessible from p-toluidine, by oxidation with aqueous permanganate solution into the p-acetoamino-benzoic acid and this latter compound then being saponified through treatment with a concentrated or dilute hydrochloric acid [Hofmann, Ber. 9 (1876), 1299; Kaiser et al., Ber. 18 (1885), 2942; Ullmann et al, Ber. 36 (1903), 1797; Meisenheimer et al. Liebigs Ann. 423 (1921), 87; see also: Kremer, Journ. Chem. Educ. 33 (1956), 71].

From the Netherlands published patent specification No. 6,415,195, it is known to produce p-aminobenzoic acid from 4-(hexafluoro-2-hydroxy-2-propyl)-aniline by treatment with potassium hydroxide in diglycol as a solvent medium.

Finally, there may still be mentioned the formation of p-aminobenzoic acid by heating 4-bromo-aniline with copper cyanide, potassium cyanide and alcohol at 220°C. [Rosenmund et al., Ber. 52 (1919), 1752], and the direct amination of benzoic acid with $NH_2OH—FeSO_4$ [C.A. 61 (1964), 1789] or under the effect of gamma rays [C.A. 69 (1968), 112147 and C.A. 70 (1969), 119980].

For carrying out a large scale industrial or commercial production of p-aminobenzoic acid, only those processes for the reduction of p-nitrobenzoic acid have been previously considered as having any value. These processes, however, are accompanied by considerable disadvantages. Thus, p-nitrobenzoic acid is usually obtained by nitration of toluene and then oxidation of the resulting p-nitro-toluene. However, the nitration does not proceed selectively but instead leads to a mixture of o- and p-isomers which must then be worked up and isolated by means of fractional crystallization. Also, the oxidation which is usually carried out with hydrogen peroxide or manganese dioxide or by electrochemical means, requires considerable expense. This is also true of the subsequent reduction which is most often accomplished by means of iron with hydrochloric acid. Over all of the stages of such an industrial reaction, the process is regarded as being excessively long, costly to run, and having only a slight selectivity so that one can obtain only very low yields.

One object of the present invention is to provide a process for producing para-aminobenzoic acid in a relatively simple manner with a high selectivity and very good yields from monoester derivatives of terephthalic acid which are relatively cheap and available in large quantities as industrial by-products. It is also an object of the invention to provide a two stage process in which a first stage ammonolysis of the monoester is readily combined with a second stage. Hofmann reaction to permit a very efficient conversion of the original monoester reactant into the desired para-aminobenzoic acid.

Thus, it has now been found, in accordance with the invention, that these objects are achieved in an improved method of producing p-aminobenzoic acid by the steps comprises:

1. reacting ammonia, which contains not more than 15% by weight of water, in the liquid phase at temperatures of 50° to 132°C. and at an ammonia pressure of 20 to 115 atmospheres in a first stage with at least one monoester reactant of the formula

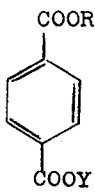

wherein

R is methyl, ethyl, propyl, isopropyl, butyl, isobutyl, phenyl,

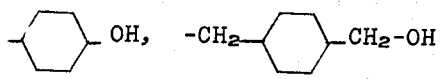

or —$CH_2CH_2$—OH, and

Y is hydrogen, sodium, lithium, magnesium, calcium or ammonium, with the proviso that where y is sodium, the reaction mixture also contains at least a catalytic amount of the monomethyl terephthalate or monoglycol terephthalate;

2. substantially removing ammonia from the resulting terephthalic acid monoamide intermediate product including any ammonia present in the form of ammonium ions; and 3. subjecting the ammonia free monoamide product to the Hofman reaction in a second stage to obtain the p-aminobenzoic acid product.

The monomethyl ester of terephthalic acid arises as a byproduct in the production of dimethyl terephthalate which is required in very large quantities in the synthetic fiber industry for the manufacture of polyester fibers, e.g. polyethylene terephthalate fibers or yarns, the same polyesters also being used to make films or molded products. The various salts can be obtained in a simple manner by neutralization of the monomethyl-terephthalate with the hydroxide of lithium, sodium, calcium, magnesium or ammonium. For economical reasons and as an industrial process, it is preferable to use as the monoester reactant the free monomethyl ester of terephthalic acid.

The ammonia employed in the first stage can contain water up to 15% by weight. It has been determined that the yield of the terephthalic acid monoamide or its corresponding salt as the intermediate product decreases with an increasing water content of the ammonia. The presence of water in the first stage reaction not only prevents a complete ammonolysis at the prescribed reaction conditions but also causes a saponification of the resulting terephthalic acid monoamide. Accordingly, depending upon its water content, the reaction mixture obtained in the first stage of the process of the invention contains, besides the named salts of the terephthalic acid monoamide, also more or less amounts of ammonium terephthalate as an undesirable by-product. The ammonia is therefore preferably used in this invention with a water content of not more than 5% by weight and, most advantageously, not more than 1% by weight. Under these conditions, only very slight amounts of saponification products will form. Since technical ammonia is generally available with less than 1% by weight of water, this commercial grade of ammonia is most suitable for purposes of the present invention.

The ammonolysis of the monoester of terephthalic acid and/or its salts in the first stage is carried out in the liquid phase at an elevated temperature of about 50°C. to 132°C. and under ammonia pressures, of about 20 to 115 atm. This means that at least part of the ammonia must be present in liquid form. At temperatures below about 70°C., the reaction speed is usually too low so that the ammonolysis is preferably accomplished at temperatures in the range of 70° to 120°C. and at corresponding ammonia pressures of about 30 to 100 atm. The ammonia can be introduced in stoichiometric amounts with reference to the formation of the monoamide intermediate. As a practical matter, however, this stoichiometric amount would not be sufficient in a given reaction zone to achieve the necessarily high ammonia pressures, and the ammonia is therefore preferably introduced in an excess of up to about 35 mols per mol of the monoester reactant of the first stage. The most preferred molar ratio of ammonia:monoester is about 5:1 to 30:1.

By using the preferred reaction conditions, the reaction time for the first stage is about 0.5 to 10 hours.

One may proceed as follows in carrying out the first stage ammonolysis. First, the monoester reactant as the free acid, the appropriate salt or suitable mixtures of reactants is placed into an autoclave to which there is also added liquid ammonia of the required low water content. This essential reaction mixture is then heated to the desired reaction temperature which then also determines the ammonia partial pressure within the closed vessel. After the first stage reaction has taken place, the autoclave is opened or released to normal (atmospheric) pressure. Excess ammonia and any methanol split off during the reaction escapes hereby in the form of vapor. Both vapors or gases can be fractionally condensed and used again, e.g. the methanol being used in the preparation of mono- or dimethyl terephthalate while the ammonia can be easily reused for the initial ammonolysis stage of the invention.

It has been found that in using the lithium, calcium or magnesium salts of the terephthalic acid monoester, there is a very distinct catalytic acceleration of the reaction provided that the ammonium salt of the monomethyl- or monoglycol-terephthalate or mixtures thereof is added to the mixture in at least a catalytic amount. This is especially of value in using the calcium salt of the monoester reactant. Of course, if the cited lithium, calcium and/or magnesium salts are used in admixture with monomethyl- and/or monoglycol-terephthalate, then the addition of the specific catalysts can be avoided because they are formed in situ, i.e. the monoester with its free carboxylic group immediately forms with the ammonia reactant the corresponding catalytically effective ammonium salt.

If sodium-monomethylterephthalate or sodium-monoglycolterephthalate are treated under the given temperature and pressure conditions with liquid ammonia, there is practically no ammonolysis. However, as in the case of the lithium, calcium and magnesium salts, when the sodium salts are used in admixture with the monomethyl- and/or monoglycol-terephthalate, good yields of the corresponding salts of terephthalic acid monoamide are obtained. Surprisingly, it was found that even with only catalytic amounts of the ammonium monomethyl- and/or monoglycol-terephthalate, a complete ammonolysis is effective. In general, catalytic amounts represent up to about 0.10 mol and preferably 0.01 to 0.10 mol per mol of the monoester reactant.

In place of the above-noted terephthalic acid monoesters or the cited salts, the process of the invention may be extended to still other terephthalic acid monoesters, e.g. other aliphatic, cycloaliphatic, araliphatic or aryl monoesters, principally the monophenyl ester or its salt derivatives. However, from a practical or commercial viewpoint, monoesters other than the monomethyl ester are at the present time much less easily accessible so that the process of the present invention is especially preferred for use with the terephthalic acid monomethyl ester and its named salts.

The resulting reaction mixture at the end of the reaction in the first stage consists essentially of the ammonium salt of terephthalic acid monoamide when the initial monoester reactant is in the acid form or the ammonium salt form. When there is an initial addition of the sodium, lithium, magnesium and/or calcium salts of the monoester reactant, e.g. of the monomethyl-terephthalate, the final reaction mixture of the first stage consists essentially of the corresponding metal salts of the terephthalic acid monoamide and slight amounts of the ammonium salt of the monoamide formed by resalting. If one uses mixtures of the monoester reactant in its acid form together with at least one salt other than the ammonium salt, then the reaction mixture yields the intermediate terephthalic acid monoamide in salt form with the ammonium salt corresponding approximately to the initial terephthalic acid monoester in its free acid form. Thus, in all cases, one can expect to find some ammonium salt of the intermediate monoamide product in the reaction mixture obtained in the first stage of the process according to the invention.

This first stage reaction mixture is worked up as follows. The solid monoamide product, which is left after removing liquid ammonia and any other volatile components such as methanol, can first be digested or dissolved in about 5 to 10 times as much water with a dilute or half-strength mineral acid, such as hydrochloric or sulfuric acid, being added up to the point where the terephthalic acid monoamide precipitates quantitatively. This usually occurs at a pH of approximately 3, i.e. at pH-values on the order of 2 to 4. The resulting acid monoamide can then be filtered off or centrifuged, washed with water and/or acetone and finally dried. The resulting crude product melts above 350°C. It does not require any further purification but can be used directly in the generally well-known Hofmann reaction.

On the other hand, one can also proceed at the end of the first stage by dissolving or digesting the monoamide product in 5 to 10 times as much water, and then expelling the ammonia which may be present in the form of ammonium ions through resalting as well as in the form of adherent ammonia, by adding a slight excess of an alkali metal hydroxide or alkaline earth metal hydroxide at temperatures below 25°C. Air at about room temperature can also be passed through the resulting solution to ensure the removal of the ammonia. The resulting ammonia-free solution of the monoamide intermediate can then be used directly for the second stage Hofmann reaction.

The Hofmann reaction is a general reaction in which a carboxylic acid amide is reacted with a hypochlorite or hypobromite so as to be converted to the primary amine containing one less carbon atom. See, for example: Wallis and Lane, Organic Reactions, Vol. 3 (1946), pages 267ff; Franzen, Chem. Ztg., Vol. 80 (1856), pages 8ff; Fieser & Fieser, Organic Chemistry, Reinhold Publ. Corp. (1961), pp. 499–501, 523; and Henrichsen et al., Organic Chemistry, McGraw-Hill (1970), pp. 704–706. In this Hofmann reaction, a hydrogen atom of the amide group is first replaced by the halogen (chlorine or bromine) as illustrated by the following reaction sequence as the first phase of the reaction:

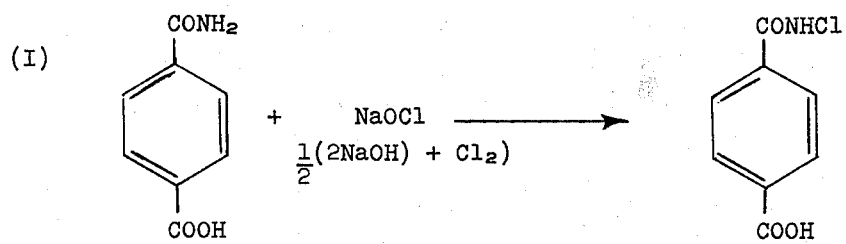

The resulting acid N-halogenamide forms with the alkali an unstable salt whose anion splits off the halogen as a halide ion. This results in an intermediate which is rearranged to the isocyanate which finally under the effect of the alkali hydroxide (NaOH) is converted into the amine with a release of carbon dioxide, all as set forth in the second phase of the Hofmann reaction:

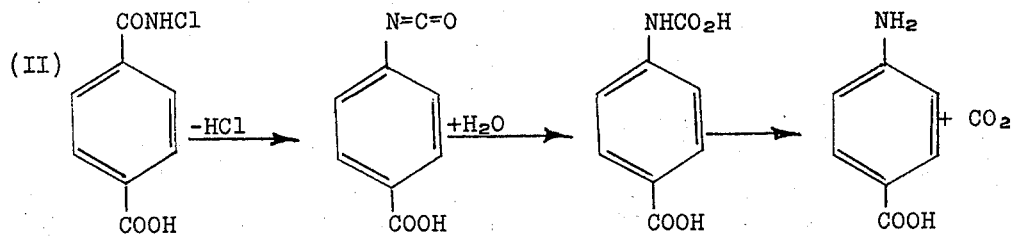

For carrying out the Hofmann reaction in the process of the present invention, useful hypohalites are the hypochlorite and hypobromite of the metals sodium, potassium, calcium and barium. The corresponding hypohalites of rubidium, lithium, cesium and strontium are also suitable but generally will not be used because of their excessively high price. Since the hypochlorites are usually cheaper than the hypobromites, the Hofmann reaction of the present invention is preferably carried out with the hypochlorites of sodium, potassium, calcium and/or barium.

In the Hofmann reaction, one molar equivalent of hypohalite is theoretically needed per mol of terephthalic acid monoamide. Good results have been achieved in the present invention with a molar equivalent ratio of hypohalite:monoamide of 0.8:1 to 1.2:1. A larger excess of the hypohalite is to be avoided because under these conditions, undesirable oxidation products of the p-aminobenzoic acid may be formed. One preferably uses the stoichiometric ratio of 1:1.

Theoretically, a total of 5 molar equivalents of hydroxide per mol of the terephthalic acid monoamide is necessary in the Hofmann reaction of the free terephthalic acid monoamide, i.e. for neutralization, for forming the hypohalite and for splitting or cleaving the isocyanate group. It has been proven in the present invention, that an excess of the hydroxide favorably influences the selectivity with reference to the formation of the desired p-aminobenzoic acid. Accordingly, there is preferably employed a molar ratio of hydroxide:- monoamide of about 5:1 to 6:1.

The conversion of the terephthalic acid monoamide in the second stage of the present invention according to the Hofmann reaction can be carried out in different ways. For example, the hypohalite can be separately prepared wherein the calculated amount of chlorine or bromine is conducted or added dropwise at 0°-5°C. to about about one-half of the total amount of aqueous alkaline solution required. This hypohalite solution can then be joined with the monoamide in the remainder of the alkaline solution. It is also possible, however, to dissolve the terephthalic acid monoamide directly into the entire amount of alkaline solution and then to lead the halogen (chlorine or bromine) into this solution at 0°-5°C.

During the first phase (I) of the Hofmann reaction for the formation of the N-halogenamide, a temperature of about 0°-15°C. and preferably 0°-5°C. is maintained in the reaction vessel. The use of higher temperatures for this first phase should be avoided because it can lead to the formation of undesirable by-products and a reduction in yield. The course of the N-halogenamide formation can be easily followed in the change of the redox potential. The end of the first phase "halogenation" will be recognized by the appearance of a constant potential. The rearrangement or transposition of the N-halogenamide is carried out at higher temperatures and begins at about 20°C. to 30°C. Preferably, this second phase of the Hofmann reaction is carried out at a temperature of about 20°C. to 90°C. The rearrangement is ordinarily completed after about 3 to 30 minutes, depending upon the temperature.

In other respects, one can employ those measures or process conditions which are conventional in all Hofmann reactions. The process can also be carried out continuously with good results. One advantageously proceeds adiabatically while using a so-called "plug-flow" reactor. By maintaining the preferred reaction conditions, yields of over 99% of theory can be achieved.

After completion of the Hofmann reaction, a yellow to light brown colored solution is obtained as the initial product. The p-aminobenzoic acid is easily precipitated by acidifying this product solution up to the isoelectric point at a pH-value of about 4. The precipitate can be filtered off or centrifuged, then washed with a little cold water and finally dried. The initial "crude" product melts at 185°-187°C. and it can be even further purified by recrystallization in water.

Para-aminobenzoic acid belongs to the B-vitamin group, and it is often used as a stabilizer for various cosmetic products. In the pharmaceutical art, it is of special interest for the preparation of important anesthetics, e.g. Anestesin, Novocain and Pantocain. Furthermore, p-aminobenzoic acid is often introduced in the preparation of special polyamide fibers, e.g. poly-p-benzamide. It is also used in the manufacture of azo dyes and in sunburn preventives.

The first 12 examples which follow are directed to the novel first stage of the process of the invention, including the production of the terephthalic acid monoamide or its salt as well as the conversion of the salt into the free acid form of the monoamide.

EXAMPLE 1

9 grams (0.05 mols) of monomethyl-terephthalate and 21.2 grams (1.25 mols) of liquid ammonia were placed into a 100 ml. V4A-autoclave (lined with a steel alloy). Under intensive mixing by means of a magnetic stirrer, this mixture was heated within about 15 minutes up to 110°C. so that the reaction pressure then amounted to approximately 75 atmospheres gauge. After 10 hours reaction time under these conditions of temperature and pressure, the autoclave was cooled and released to normal pressure. The reaction product, a powdery white substance, was dissolved in 200 ml. of water. By acidifying this solution with a half concentrated hydrochloric acid (up to a pH of 3), a pure white product precipitated out from the solution and was filtered off. This residue was then washed with 400 ml. each of water and acetone, and the product dried at 70°C. under vacuum. The final product was 7.9 grams of terephthalic acid monoamide (96.1% of theory).

EXAMPLE 2

9.3 grams (0.05 mols) of lithium-monomethylterephthalate was subjected to the liquid phase ammonolysis as described in Example 1 with 21 grams of liquid ammonia. The reaction temperature was 120°C. with a pressure of about 90 atm, and the reaction time was 10 hours. The residue or solid reaction product was suspended in water and acidified with hydrochloric acid to a pH-value of 3. After filtration, washing with water and acetone and then drying as in Example 1, there remained 6.5 grams (79.0% of theory) of pure terephthalic acid monoamide.

EXAMPLE 3

9.3 grams (0.05 mols) of lithium-monomethylterephthalate and 0.4 grams (0.002 mols) of ammonium-monomethylterephthalate were reacted with 22 grams of liquid ammonia in the same manner as in Examples 1 and 2 at 120°C., 90 atm. and for a period of 10 hours, thereafter isolating the resulting terephthalic acid monoamide as in the preceding examples. The yield amounted to 7.8 grams (95% of theory with reference to the initial lithium compound).

EXAMPLE 4

10.1 grams (0.025 mols) of magnesium-monomethyl-terephthalate were subjected to the liquid phase ammonolysis with 21 grams of liquid ammonia in the same manner as in the preceding examples. The reaction temperature was 120°C., the pressure was 90 atm. and the reaction period was only 3 hours in this instance. The solid reaction product remaining after releasing the pressure was suspended in water and acidified to a pH-value of 3 with hydrochloric acid. The resulting precipitate was filtered off, washed with water and acetone and then dried as in the preceding examples. There was obtained 8.0 grams (96.2% of theory) of the terephthalic acid monoamide.

EXAMPLE 5

10.1 grams (0.025 mols) of magnesium-monomethyl-terephthalate were reacted for 10 hours with 21.2 grams of liquid ammonia and then worked up as in the preceding examples. There resulted 8.2 grams (99.1% of theory) of the desired terephthalic acid monoamide.

EXAMPLE 6

11 grams (0.025 mols) of calcium-monomethyl-terephthalate were brought together with 1 gram (0.005 mols) of ammonium-monomethylterephthalate as a catalyst and 22 grams of liquid ammonia for a period of 10 hours at 120°C. and 90 atm. to carry out the ammonolysis reaction. After working up the solid product as in the preceding examples, there remained 8.2 grams of terephthalic acid monoamide, corresponding to a yield of 99.1% of theory (with reference to the initial calcium-monomethylterephthalate). In the absence of the ammonium-terephthalate catalyst, the yield achieved under otherwise the same conditions amounted to only 42.2% of theory.

EXAMPLE 7

4.7 kg. (26 mols) of monomethylterephthalate and 10 kg. of liquid $NH_3$ were placed in a 40-liter electrically heated rotatable autoclave lined with V4A-steel alloy. The rotated autoclave was then heated up to 120°C. within about 7 hours and then maintained at this temperature for another 8 hours. The reaction pressure amounted to 92 atm. at this temperature. The autoclave was then cooled and released to normal pressure. The solid product was first dissolved in water, and then the terephthalic acid monoamide was precipitated out by addition of a half concentrated hydrochloric acid. The product was filtered off, washed first with approximately 10 liters of water and then further washed with 3 liters of acetone. After drying under vacuum at 70°C., there remained 3950 grams of pure terephthalic acid monoamide (92% of theory).

EXAMPLE 8

10.5 grams (0.05 mols) of monoglycolterephthalate was subjected to the liquid phase ammonolysis with 23 grams of liquid ammonia in the same manner as in Example 1. The reaction temperature amounted to 120°C., the pressure was 90 atm. and the reaction period lasted for 10 hours. The solid residue of the reaction was dissolved in water and acidified with hydrochloric acid as in the preceding examples. After filtration, washing with water and acetone and then drying at 70°C. under vacuum, the pure terephthalic acid monoamide was obtained in an amount of 8.0 grams (97% of theory).

EXAMPLE 9

9.5 grams (0.05 mols) of sodium monomethylterephthalate and 0.4 grams (0.0002 mols) of ammonium monomethylterephthalate as a catalyst were reacted with 22 grams of liquid ammonia according to the manner described in Example 1 at 120°C. and 90 atm. and for a period of 15 hours. The resulting terephthalic acid monoamide was then isolated as in the preceding examples. The yield was 7.3 grams (89% of theory with reference to the initial sodium compound).

EXAMPLE 10

9.7 grams (0.05 mols) of monoethylterephthalate and 25.8 grams of liquid ammonia were heated under stirring up to 110°C. in a 100 ml. V4A-autoclave, whereby a pressure of 75 atm. gauge was attained, the reaction then being carried out at these conditions for a period of 12 hours. Thereafter, the autoclave was cooled and released to normal pressure (1 atm.). The reaction product was dissolved in 200 ml. of water and then acidified to a pH-value of 3 with half concentrated hydrochloric acid (i.e. a half-strength concentrated HCl, e.g. a 17.5% by weight HCl solution in water). A pure white product precipitated out. After filtering off this product and drying at 70°C. under vacuum, there remained 7.8 grams (95% of theory) of pure terephthalic acid monoamide.

EXAMPLE 11

6.0 grams (0.025 mols) of monophenylterephthalate were brought together with 26.2 grams of liquid ammonia for reaction under the same conditions specified in Example 10. After working up the product as in all of the preceding examples, there were obtained 4.1 grams (99% of theory) of terephthalic acid monoamide.

EXAMPLE 12

6.6 grams (0.025 mols) of the terephthalic acid monocyclohexane-(1,4)-diol ester were brought together with 25 grams of liquid ammonia for reaction at 120°C. and 85 atm. gauge for 65 hours. After working up the product as in the preceding examples, the yield of the terephthalic acid monoamide amounted to 3.25 grams (79% of theory).

The next five examples are directed to the second stage of the process of the invention, i.e. the production of the p-aminobenzoic acid by conversion of the intermediate terephthalic acid monoamide according to the Hofmann reaction.

EXAMPLE 13

35.3 grams (0.214 mols) of terephthalic acid monoamide were dissolved at 5°C. in a solution of 12 grams (0.3 mols) sodium hydroxide and 100 ml. of water. This solution, while being stirred and cooled, was quickly mixed with a freshly prepared sodium hypochlorite solution of 0°–5°C. previously obtained by leading 15.3 grams (0.215 mols) chlorine into a solution of 40 grams (1.0 mol) NaOH and 250 ml. of water. The resulting mixture was further stirred for 1.5 hours. Then, cooling was removed and within 10 minutes the mixture heated up to 40°C. Thereby, the reaction became initiated as evidenced by an adiabatic rise in temperature up to 65°C. The reaction product was maintained at 65°C. for 1 hour to yield a bright brown colored solution. The p-aminobenzoic acid was precipitated by acidification of the solution with hydrochloric acid to a pH-value of 4. The acid was then filtered off, washed with 50 ml. of cold water and finally dried. The yield amounted to 94.2% of theory.

EXAMPLE 14

35.3 grams (0.214 mols) of terephthalic acid monoamide were stirred while cooling at 5°C. into a suspension which had been freshly produced just before this addition by leading 15.3 grams (0.215 mols) of chlorine into a mixture of 51 grams (0.693 mols) of Ca(OH)$_2$ and 300 ml. of water. The reaction mixture was further stirred for 1.5 hours at 5°C., and then heated up to 42°C. within about 10 minutes. The reaction started at this point as evidenced by the adiabatic temperature increase. After a further 10 minutes, the temperature thereby reached 60°C. The reaction product was maintained at 60°C. for one hour and was then cooled. The reaction solution was worked up as described in Example 13. The yield of p-aminobenzoic acid amounted to 92.1% of theory.

EXAMPLE 15

35.3 grams (0.214 mols) of terephthalic acid monoamide was stirred while cooling at 5°C. into a hypochlorite solution which had been previously freshly prepared by leading 15.3 grams (0.215 mols) of chlorine into 62 grams (1.1 mols) of KOH and 300 ml. of water. The reaction mixture was maintained at 5°C. for 2 hours and then quickly heated to 45°C. After one hour at this temperature, the reaction product was cooled and worked up in the same manner as Example 13. The yield of p-aminobenzoic acid amounted to 95.0% of theory.

EXAMPLE 16

35.3 grams (0.214 mols) of terephthalic acid monoamide were stirred while cooling at 5°C. into a freshly produced sodium hypobromite solution (obtained from 44 grams NaOH, 300 ml. H$_2$O and 34.5 grams bromine). The mixture was heated up to 40°C. at which point the reaction started. The temperature rose adiabatically to 64°C. After one hour's reaction time, the mixture was cooled and p-aminobenzoic acid was separated as described in Example 13. The yield amounted to 96.2% of theory.

EXAMPLE 17

14.8 grams (0.0897 mols) of terephthalic acid monoamide were stirred while cooling at 5°C. into a freshly prepared sodium hypochlorite solution obtained from 18 grams NaOH, 200 ml. H$_2$O and 6.36 grams chlorine, the mixture being held at 5°C. for about 20 minutes. The chlorinated mixture was then transferred into a heated circulatory apparatus consisting of a glass circulating pump and a tubular glass reactor. In this apparatus, the mixture was heated within about one minute to 80°C. After 3 minutes, the reaction was completed. The reaction product was poured into dilute hydrochloric acid, and the p-aminobenzoic acid was isolated in the same manner as Example 13. The yield amounted to 11.7 grams (95.4% of theory).

The following example combines both stages of the overall reaction in an advantageous manner.

EXAMPLE 18

In accordance with Example 1 above, 9 grams (0.05 mols) of monomethylterephthalate and 25 grams of liquid ammonia were reacted in the autoclave at 110°C. After a reaction period of 10 hours, the autoclave was cooled and released to normal pressure. The reaction product (the ammonium salt of terephthalic acid monoamide) in the form of a powdery white substance was next dissolved in 50 ml. of an approximately 12% by weight caustic solution (50 grams H$_2$O + 6.8 grams NaOH), and about 50 liters of air were then introduced over a 30 minute period at room temperature and under intensive mixing.

To this reaction product freed of ammonia by the air treatment, there were admixed while cooling at 5°C. about 40 ml. of freshly prepared sodium hypochlorite solution (4 grams NaOH, 50 ml. H$_2$O and 3.55 grams Cl$_2$), and the mixture further stirred for about 1 hour at 5°C. Then, the mixture was slowly heated up to 50°C. and maintained at this temperature for 1 hour. The reaction product was then worked up as in Example 13 to obtain p-aminobenzoic acid in a yield of 6.2 grams (90% of theory with reference to the initial monomethylterephthalate reactant used in the first stage).

Similar high yields in this two stage process may also be obtained by using the other initial reactants and proceeding directly from the first stage to the second stage without any extensive intermediate steps such as purification or the like, it being relatively easy to remove any excess or undesirable ammonia as the only intermediate step of the invention. At the same time, both the intermediate and final products are produced with excellent purity as well as high yields so that the overall process is of particular value for a large scale commercial production of p-aminobenzoic acid.

The invention is hereby claimed as follows:

1. A process for the production of p-aminobenzoic acid which comprises:
   reacting ammonia, which contains not more than 15% by weight of water, in the liquid phase at temperatures of 50° to 132°C. and at an ammonia pressure of 20 to 115 atmospheres in a first stage with at least one monoester reactant of the formula

wherein
   R is methyl, ethyl, propyl, isopropyl, butyl, isobutyl, phenyl,

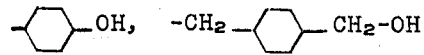

or —CH$_2$CH$_2$—OH, and
   Y is hydrogen, sodium, lithium, magnesium, calcium or ammonium, with the proviso that where Y is sodium, the reaction mixture also contains at least a catalytic amount of the monomethyl terephthalate or monoglycol terephthalate;
   substantially removing ammonia from the resulting terephthalic acid monoamide intermediate product including any ammonia present in the form of ammonium ions; and
   subjecting the ammonia free monoamide product to the Hofmann reaction in a second stage to obtain the p-aminobenzoic acid product.

2. A process as claimed in claim 1 wherein the water content of the ammonia in said first stage reaction is not more than about 5% by weight.

3. A process as claimed in claim 1 wherein the water content of the ammonia in said first stage reaction is not more than about 1% by weight.

4. A process as claimed in claim 1 wherein the first stage reaction with ammonia is carried out at a temperature of between about 70°C. and 125°C. and an ammonia pressure of between about 30 and 100 atmospheres.

5. A process as claimed in claim 1 wherein the first stage reaction is carried out with ammonia in an amount of about 5 to 30 mols per mol of the monoester reactant.

6. A process as claimed in claim 1 wherein the second stage Hofmann reaction is carried out by using a hypochlorite or hypobromite of sodium, potassium, calcium or barium for reaction with the monoamide intermediate product.

7. A process as claimed in claim 6 wherein sodium hypochlorite is used in the Hofmann reaction.

8. A process as claimed in claim 6 wherein the hypochlorite or hypobromite is employed in an approximately stoichiometric ratio of hypohalite:monoamide of 1:1.

9. A process as claimed in claim 6 wherein the Hofmann reaction is carried out with a molar ratio of hydroxide:monoamide of about 5:1 to 6:1.

10. A process as claimed in claim 6 wherein the first phase of the Hofmann reaction, in which there preponderantly occurs an N-halogenamide intermediate, is carried out at a temperature of 0° to 15°C.

11. A process as claimed in claim 10 wherein said temperature of the first phase of the Hofmann reaction is maintained at about 0°C. to 5°C.

12. A process as claimed in claim 6 wherein the second phase of said Hofmann reaction, in which the rearrangement of the N-halogenamide occurs, is carried out at a temperature of about 20°C. to 90°C.

13. A process as claimed in claim 1 wherein the monoester reactant of the first stage is in the form of the lithium, calcium or magnesium salt admixed with the ammonium salt of monomethylterephthalate or monoglycolterephthalate as a catalyst in a molar ratio of up to 0.10 mols of catalyst per mol of the reactant.

14. A process as claimed in claim 1 wherein the monoester reactant of the first stage is in the form of the sodium salt admixed with the ammonium salt of monomethylterephthalate or monoglycolterephthalate as a catalyst in a molar ratio of up to 0.10 mols of catalyst per mol of the reactant.

15. A process as claimed in claim 1 wherein the monoester reactant is monomethylterephthalate, the sodium, lithium, calcium, magnesium or ammonium salt of said monomethylterephthalate or mixtures thereof.

16. A process as claimed in claim 1 wherein the monoester reactant is monomethylterephthalate.

* * * * *